[54] SUBSTITUTED 5-(PHENOXYALKYL)-3-PHENYL-3-(1H-IMIDAZOL-1-YLMETHYL)-2-METHYLISOXAZOLIDINES

[75] Inventors: Vassil St. Georgiev, Rochester; George B. Mullen, Avon, both of N.Y.

[73] Assignee: Pennwalt Corporation, Philadelphia, Pa.

[21] Appl. No.: 900,851

[22] Filed: Aug. 27, 1986

[51] Int. Cl.$^4$ ............................................. C07D 233/60
[52] U.S. Cl. .................................... 548/240; 548/335; 568/630; 564/123
[58] Field of Search ............................................ 548/240

[56] References Cited

U.S. PATENT DOCUMENTS 3,711,495  1/1973  Kulsa et al. ........................ 548/240
3,915,978  10/1975 Kulsa et al. ........................ 548/240
3,987,179  10/1976 Nadelson ............................ 514/378

FOREIGN PATENT DOCUMENTS 54-76579  6/1979  Japan.

OTHER PUBLICATIONS

Sokolov, S. V. et al., Chemical Abstract 55:7399 (1961), Abstracting "Isoxazle Compounds III, Synthesis of Some Isoxazolylazoles", Zhur. Obshchei Khim. 30, pp. 1781–1787 (1960).
Kano, H. et al., Chem. Abstract 62:9139a (1965). Abstracting French 1,376,432 (Oct. 23, 1964).
Kano, H. et al., Chemical Abstract 63:8367a (1965). Abstracting French 1,380,177 (Nov. 27, 1964).
Takahi, Y. et al., Chemical Abstract 81:22233c (1974). Abstracting Japan Kokai 7,399,336 (Dec. 15, 1973).
Boyce, C. B. et al., Chemical Abstract 87:23258a (1977). Abstracting German Offen. 2,639,189 (Mar. 10, 1977).
Funaki, Y. et al., Chemical Abstract 92:128915u (1980). Abstracting Japan Kokai 79 76,579 (Jun. 19, 1979).

Primary Examiner—Donald G. Daus
Assistant Examiner—Barbara Cassatt

[57] ABSTRACT

Substituted 5-(phenoxyalkyl)-3-phenyl-3-(1H-imidazol-1-ylmethyl)-2-methylisoxazolidines, in which hydrogens of their benzene rings may be replaced by halogen, lower alkoxy, lower alkyl, nitro, acetamido and/or trifluoromethyl groups, are useful as antifungal agents.

29 Claims, No Drawings

SUBSTITUTED 5-(PHENOXYALKYL)-3-PHENYL-3-(1H-IMIDAZOL-1-YLMETHYL)-2-METHYLISOXAZOLIDINES

BACKGROUND OF THE INVENTION

This invention pertains generally to substituted 2-methylisoxazolidines and more specifically to substituted 5-(phenoxyalkyl)-3-phenyl-3-(1H-imidazol-1-ylmethyl)-2-methylisoxazolidines which are useful as antifungal agents.

BRIEF SUMMARY OF THE INVENTION

In accordance with this invention there are provided compounds of the formula:

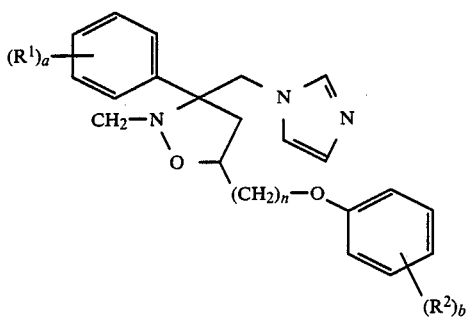

and the pharmaceutically acceptable acid addition salts thereof, in the form of their enantiomers or mixtures of their enantiomers including diastereoisomeric pairs of such enantiomers, wherein;

a = 1 or 2,
b = 1 or 2,
$R^1$ is selected from hydrogen, lower alkyl, lower alkoxy, halogen, and combinations thereof, provided that the ortho position is hydrogen,
$R^2$ is selected from hydrogen, lower alkyl, lower alkoxy, halogen, trifluoromethyl, nitro, acetamido, and combinations thereof, and
The alkyl moiety $(CH_2)n$ represents a branched or unbranched chain where n = 1 to 8.

DETAILED DESCRIPTION OF THE INVENTION

The compounds of this invention are useful as antifungal agents. They have been shown to have activity against yeast and systemic mycoses and dermatophytes as determined by broth and agar testing techniques [McGinnis, M. R., *Laboratory Handbook of Medical Mycology*, Academic Press, N.Y., N.Y. (1980)]. The compounds prepared in Examples 1-14, 16-18 and 22-27 below were tested and found to have good to moderate inhibitory activity against a broad spectrum of organisms including trichophyton mentagrophytes, trichophyton tonsurans, trichophyton schoenleinii, epidermophyton floccosum and candida stellatoidea (minimum inhibitory concentration, MIC, of <0.2 to 70 ug/ml).

Because of the antifungal activity of the compounds of the invention they can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

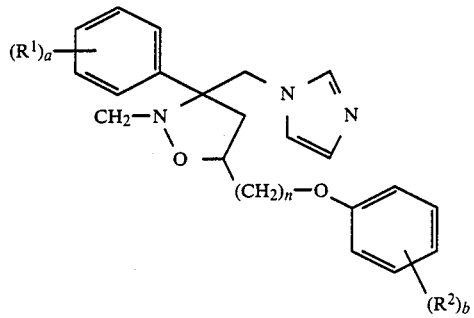

and the pharmaceutically acceptable acid addition salts thereof, in the form of their enantiomers or mixtures of their enantiomers including diastereoisomeric pairs of such enantiomers, wherein;

a = 1 or 2,
b = 1 or 2,
$R^1$ is selected from hydrogen, lower alkyl, lower alkoxy, halogen, and combinations thereof, provided that the ortho position is hydrogen,
$R^2$ is selected from hydrogen, lower alkyl, lower alkoxy, halogen, trifluoromethyl, nitro, acetamido, and combinations thereof, and
The alkyl moiety $(CH_2)n$ represents a branched or unbranched chain where n = 1 to 8.

By halogen is meant chlorine, bromine, fluorine and iodine with chlorine and fluorine being preferred. By lower alkyl and lower alkoxy is meant $C_1$ to $C_4$ which can be a branched or unbranched chain. Compounds having ortho substitution of the upper phenyl group were not prepared probably due to steric hindrance.

The 5-(phenoxyalkyl)-3-phenyl-3-(1H-imidazol-1-ylmethyl)-2-methylisoxazolidines are obtained as mixtures of cis- and trans-diastereomers due to the presence in the isoxazolidine ring of two asymmetric carbon atoms. The diastereomeric mixture is conveniently separated by flash-chromatography on silica gel using halogenated hydrocarbons (preferably dichloromethane and chloroform), alkanols (preferably methanol and ethanol), ethyl acetate and such as eluents. The eluents may be utilized alone or in combinations such as the ones comprised of 95-99% by volume halogenated hydrocarbon and 1-5% by volume alkanol. The stereochemistry of the two asymmetric carbon atoms in the isoxazolidine ring may be determined by conventional methods that include X-ray crystallography, nuclear magnetic resonance spectroscopy, circular dichroism or optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−)-tartaric acid, (+) and (−)-dibenzoyltartaric acid and the like.

As illustrated in the following diagrams, the compounds can be prepared starting with the reaction of 2-(1H-imidazol-1-yl)acetophenones 1 with N-methylhydroxylamine to give the corresponding nitrone derivatives 2 which are the subject matter of our concurrently filed copending application Ser. No. 900,856 entitled "α-Substituted Ketonitrone Derivatives" whose disclosure is incorporated herein by reference. In one synthesis scheme, the latter derivative is treated with an appropriate allyl phenyl ether compound 3 to provide a diastereomeric mixture of the desired cis- and trans-substituted 5-(phenoxymethyl)-3-phenyl-3-(1H-imidazol-1-ylmethyl)-2-methylisoxazolidine derivative 4. Alternatively, reaction of the nitrone compound 2 with an appropriate 1-(ω-alkenyloxy)benzene derivative (5) leads to the corresponding diastereomeric mixture of cis- and trans-substituted 5-[(ω-phenoxy)alkyl]-3-phenyl-3-(1H-imidazol-1-ylmethyl)-2-methylisoxazolidine compound 6 (n>1).

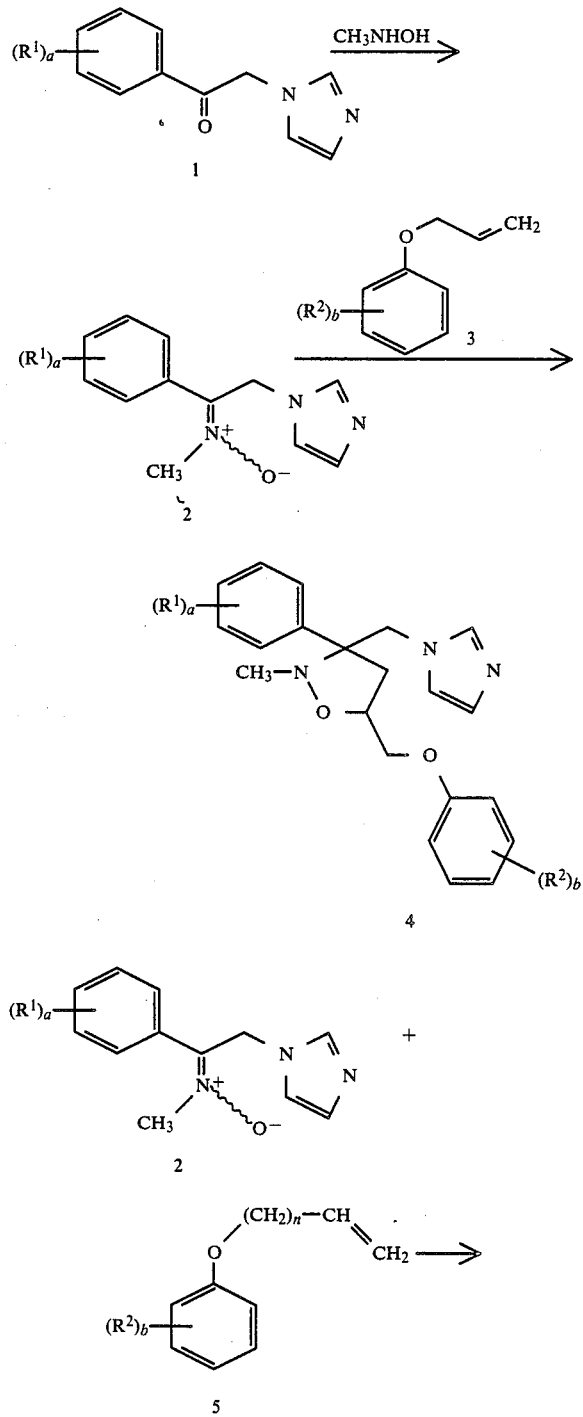

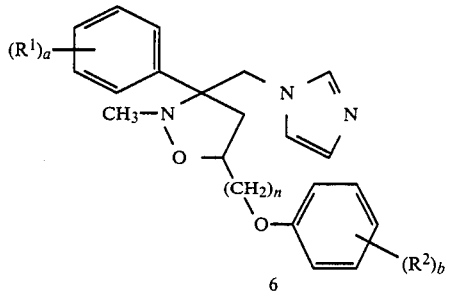

The compounds of the invention are basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following synthesis of intermediates and in the Examples. Unless otherwise indicated, n=1.

PREPARATION OF IMIDAZOLYLACETOPHENONES (1)

The imidazolylacetophenone compounds 1 are prepared according to known procedures, for example, (a) Godefroi et al., J. Medicinal Chem. 12, 784 (1969) and (b) Nardi et al., J. Medicinal Chem. 24, 727 (1981).

The following imidazolyacetophenones 1 were synthesized:

(1) 2-(1H-imidazol-1-yl)acetophenone, mp 117°–119° C., (2) 2-(1H-imidazol-1-yl)-4'-chloroacetophenone 152°–156° C., (3) 2-(1H-imidazol-1-yl)-4'-methylacetophenone, mp 133°–137° C., (4) 2-(1H-imidazol-1-yl)-4'-methoxyacetophenone, mp 134°–137° C., (5) 2-(1H-imidazol)-1-yl)-4'-fluoroacetophenone, mp 150°–155° C., (6) 2-(1H-imidazol-1-yl)-3',4'-dichloroacetophenone, mp 124°–126° C., (7) 2-(1H-imidazol-1-yl)-4'-chloro-3'-methylacetophenone, mp 116°–118° C., (8) 2-(1H-imidazol-1-yl)-3'-methoxyacetophenone, mp 111°–113° C., and (9) 2-(1H-imidazol-1-yl)-3'-methylacetophenone.

PREPARATION OF ALLYL PHENYL ETHER COMPOUNDS (3)

The allyl phenyl ether compounds 3 are made by standard procedures [(a) White et al., J. Am. Chem. Soc. 80, 3271 (1958), (b) Tarbell and Wilson, J. Am. Chem. Soc. 64, 1066 (1942), (c) Mirek, Zesz. Nauk Univ. Jagiellon, Pr. Chem., No 9, p. 77 (1964), and (c) McBee and Rapkin, J. Am. Chem. Soc. 73, 2375 (1951)] from appropriately substituted phenols and allyl bromide. The following allyl phenyl ether derivatives were prepared:

(1) allyl 4-chlorophenyl ether, bp 55°–60° C. (0.05 Torr), (2) allyl 4-methylphenyl ether, bp 45°–47° C. (0.3 Torr), (3) allyl 4-methoxyphenyl ether, bp 65°–68° C. (0.2 Torr),
(4) allyl 4-acetamidophenyl ether, mp 90°–94° C.,
(5) allyl 2-nitrophenyl ether, bp 92°–99° C. (0.15 Torr),
(6) allyl 2,4-dichlorophenyl ether, bp 62°–65° C. (0.05 Torr),
(7) allyl 2,6-dichlorophenyl ether, bp 45°–50° C. (0.05 Torr),
(8) allyl 4-fluorophenyl ether, bp 35°–37° C. (0.025 Torr), and
(9) allyl 3-(trifluoromethyl)phenyl ether, bp 35°–37° C. (0.2 Torr).

The 1-(3-butenyloxy)-4-chlorobenzene (5, $R^2=4$—Cl) was prepared by the procedure of Rius-Alonso and Wain, Ann. Apl. Biol. 88, 299 (1978), as were 4-chloro-1-(4-pentenyloxy)-benzene and 4-fluoro-1-(4-pentenyloxy)benzene.

EXAMPLE 1

Preparation of
5-(4-Chlorophenoxymethyl)-3-(4-chlorophenyl)-3-(1H-imidazol-1-ylmethyl)-2-methylisoxazolidine (4, $R^1=R^2=4$—Cl)

A suspension of 2-(1H-imidazol-1-yl)-4'-chloroacetophenone (1, $R^1=4$—Cl) (19.90 g, 0.0902 mol), N-methylhydroxylamine hydrochloride (10.26 g, 0.123 mol) and sodium bicarbonate (10.37 g, 0.123 mol) in 200 ml ethanol is refluxed for 27 hours, under a nitrogen atmosphere. After cooling to room temperature, the suspension is filtered and the solvent is removed under reduced pressure. The residual orange-colored oil is dissolved in chloroform, filtered, and the solvent removed under reduced pressure. The oily residue (compound 2, $R^1=4$—Cl) is taken up in 200 ml of toluene and 22.8 g (1.50 equivalent) of 4-chlorophenyl allyl ether (compound 3, $R^2=4$—Cl) is added under a nitrogen atmosphere. The resulting solution is refluxed for 42 hours, cooled to room temperature and the solvent removed under reduced pressure. The residual dark-colored viscous oil which represents a cis- and trans-diastereomeric mixture of compound 4 ($R^1=R^2=4$—Cl) is flash-chromatographed on neutral silica gel using chloroform and methanol (in a 98:2 ratio by volume) as eluent. 18.64 g (49.4%) of the cis-isomer A is obtained by crystallization from ether. An analytical sample is prepared by crystallization from ethyl acetate, mp 126°–132° C.

Anal. Calcd for $C_{21}H_{21}Cl_2N_3O_2$: C, 60.30; H, 5.06; N, 10.04; Cl, 16.95. Found: C, 60.36; H, 5.15; N. 9.97; Cl, 17.14.

The trans-isomer B (6.28 g, 16.6%) is obtained by crystallization from isopropanol, mp 134°–137° C.

Anal. Calcd for $C_{21}H_{21}Cl_2N_3O_2$: C, 60.30; H, 5.06; N, 10.04: Cl, 16.95 Found: C, 60.36; H, 5.17; N, 9.97; Cl, 16.89.

The above preparation was repeated except that sodium acetate (20.18 g, 0.246 mol) was used to prepare the nitrone intermediate in place of sodium bicarbonate.

EXAMPLE 2

5-(4-Chlorophenoxymethyl)-3-(4-methoxyphenyl)-3-(1H-imidazol-1-ylmethyl-2-methylisoxazolidine (4, $R^1=4$—OCH$_3$, $R^2=4$—Cl)

The title compound 4 ($R^1=4$—OCH$_3$, $R^2=4$—Cl) was made by a procedure similar to that described in Example 1 by reacting 2-(1H-imidazol-1-yl)-4'-methoxyacetophenone (1, $R^1=4$—OCH$_3$) with N-methylhydroxylamine hydrochloride to form the corresponding nitrone derivative 2 ($R^1=4$—OCH$_3$), and treating the latter with 4-chlorophenyl allyl ether (3, $R^2=4$—Cl). The resulting cis- and trans-diastereomeric mixture of compound 4 ($R^1=4$—OCH$_3$, $R^2=4$—Cl) was flash-chromatographed on neutral silica gel using a 98:2 by volume mixture of chloroform and methanol as eluent.

Isomer A has a melting point of 130°–132° C. (ethyl acetate).

Anal. Calcd for $C_{22}H_{24}ClN_3O_3$: C, 63.84; H, 5.84: N, 10.15; Cl, 8.57. found: C, 63.91: H, 5.94; N, 10.21; Cl, 8.59.

Isomer B has a melting point of 36°–38° C. (ethyl acetate-hexane, in a 4:1 ratio by volume).

EXAMPLE 3

5-(4-Chlorophenoxymethyl)-3-(4-methylphenyl)-3-(1H-imidazol-1-ylmethyl)-2-methylisoxazolidine (4, $R^1=4$—CH$_3$, $R^2=4$—Cl)

Compound 4 ($R^1=4$—CH$_3$, $R^2=4$—Cl) was prepared by a procedure similar to that described in Example 1 by reacting 2-(1H-imidazol-1-yl)-4'-methylacetophenone (1, $R^1=4$—CH$_3$) with N-methylhydroxylamine hydrochloride to form the corresponding nitrone derivative 2 ($R^1=4$—CH$_3$), and treating the latter with 4-chlorophenyl allyl ether (3, $R^2=4$—Cl). The resulting cis- and trans-diastereomeric mixture of compound 4 ($R^1=4$—CH$_3$, $R^2=4$—Cl) was purified by flash-chromatography on neutral silica gel using a 97:3 by volume mixture of chloroform and methanol as eluent. The pure isomer A (4, $R^1=4$—CH$_3$, $R^2=4$—Cl) has a melting point of 143°–145° C. (ethyl acetate).

Anal. Calcd for $C_{22}H_{24}ClN_3O_2$; C, 66.41; H, 6.08; N, 10.56; Cl, 8.91. Found: C, 66.38; H, 6.09; N. 10.54; Cl, 8.91.

EXAMPLE 4

5-(4-Chlorophenoxymethyl)-3-(4-fluorophenyl)-3-(1H-imidazol-1-ylmethyl)-2-methylisoxazolidine (4, $R^1=4$—F, $R^2=4$—Cl)

Compound 4 ($R^1=4$—F, $R^2=4$—Cl) was made by a procedure similar to that described in Example 1 by reacting 2-(1H-imidazol-1-yl)-4'-fluoroacetophenone (1, $R^1=4$—F) with N-methyldroxylamine hydrochloride to form the corresponding nitrone derivative 2 ($R^1=4$—F), and treating the latter with 4-chlorophenyl allyl ether (3, $R^2=4$—Cl). The resulting cis- and trans-diastereomeric mixture of compound 4 ($R^1=4$—F, $R^2=4$—Cl) was flash-chromatographed on neutral silica gel using a 98:2 by volume mixture of chloroform and methanol as eluent.

Isomer A has a melting point of 125°–127° C. (ethyl acetate).

Anal. Calcd for $C_{21}H_{21}ClFN_3O_2$: C, 62.76; H, 5.27; N, 10.46; Cl, 8.82. Found: C, 62.92; H, 5.33; N, 10.35; Cl, 8.78.

Isomer B has a melting point of 61°–65° C. (isopropanol).

Anal. Calcd for $C_{21}H_{21}ClFN_3O_2$: C, 62.76; H, 5.27; N, 10.46; Cl, 8.82. Found: C, 62.68; H, 5.50: N, 10.36; Cl, 8.86.

EXAMPLE 5

5-(4-Chlorophenoxymethyl)-3-phenyl-3-(1H-imidazol-1-ylmethyl)-2-methylisoxazolidine (4, $R^1=H$, $R^2=4$—Cl)

Compound 4 ($R^1=H$, $R^2=4$—Cl) was prepared by a procedure similar to that described in Example 1 by reacting 2-(1H-imidazol-1-yl)acetophenone (1, $R^1=H$) with N-methylhydroxylamine hydrochloride to form the corresponding nitrone derivative 2 ($R^1=H$), and treating the latter with 4-chlorophenyl allyl ether (3, $R^2=4$—Cl). The resulting cis- and trans-diastereomeric mixture of compound 4 ($R^1=H$, $R^2=4$—Cl) was flash-chromatographed on neutral silica gel using a 98:2 by volume mixture of chloroform and methanol as eluent.

Isomer A has a melting point of 140°–142° C. (ethyl acetate).

Anal. Calcd for $C_{21}H_{22}ClN_3O_2$: C, 65.71; H, 5.78; N, 10.95; Cl, 9.24. Found: C, 65.69; H, 5.84; N, 10.85; Cl, 9.57.

Isomer B has a melting point of 141°–143° C. (ethyl acetate).

EXAMPLE 6

5-(4-Chlorophenoxymethyl)-3-(3,4-dichlorophenyl)-3-(1H-imidazol-1-ylmethyl)-2-methylisoxazolidine (4, $R^1=3,4$—$Cl_2$, $R^2=4$—Cl)

Compound 4 ($R^1=3,4$—$Cl_2$, $R^2=4$—Cl) was made by a procedure similar to that described in Example 1 by reacting 2-(1H-imidazol-1-yl)-3',4'-dichloroacetophenone (1, $R^1=3,4$—$Cl_2$) with N-methylhydroxylamine hydrochloride to form the corresponding nitrone derivative 2 ($R^1=3,4$—$Cl_2$), and treating the latter with 4-chlorophenyl allyl ether (3, $R^2=4$—Cl). The resulting cis-and trans-diastereomeric mixture of compound 4 ($R^1=3,4$—$Cl_2$, $R^2=4$—Cl) was flash-chromatographed on neutral silica gel using a 98:2 by volume mixture of chloroform and methanol as eluent.

Isomer A has a melting point of 149°–151° C. (ethyl acetate).

Anal. Calcd for $C_{21}H_{20}Cl_3N_3O_2$: C, 55.71; H, 4.45; N, 9.28; Cl, 23.49. Found: C, 55.65; H, 4.50; N, 9.21; Cl, 23.61.

EXAMPLE 7

5-Phenoxymethyl-3-phenyl-3-(1H-imidazol-1-ylmethyl)-2-methylisoxazolidine (4, $R^1=R^2=H$)

Compound 4 ($R^1=R^2=H$) was obtained by a procedure similar to that described in Example 1 by reacting 2-(1H-imidazol-1-yl)acetophenone (1, $R^1=H$) with N-methylhydroxylamine hydrochloride to form the corresponding nitrone derivative 2 ($R^1=H$), and treating the latter with phenyl allyl ether (3, $R^2=H$). The resulting cis- and trans-diastereomeric mixture of compound 4 ($R^1=R^2=H$) was flashchromatographed on neutral silica gel using a 98:2 by volume mixture of chloroform and methanol as eluent.

Isomer A has a melting point of 107°–109° C. (ethyl acetate).

Isomer B has a melting point of 165°–168° C. (isopropanol).

EXAMPLE 8

5-(3-(Trifluoromethyl)phenoxymethyl)-3-(4-chlorophenyl)-3-(1H-imidazol-1-ylmethyl)-2-methylisoxazolidine (4, $R^1=4$—Cl, $R^2=3$—$CF_3$)

Compound 4 ($R^1=4$—Cl, $R^2=3$—$CF_3$) was obtained by a procedure similar to that described in Example 1 by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl), and treating the latter with 3-(trifluoromethyl)phenyl allyl ether (3, $R^2=3$—$CF_3$). The resulting cis- and trans-diastereomeric mixture of compound 4 ($R^1=4$—Cl, $R^2=3$—$CF_3$) was flash-chromatographed on neutral silica gel using a 98:2 by volume mixture of dichloromethane and methanol as eluent.

Isomer A has a melting point of 80°–83° C. (benzene).

Anal. Calcd for $C_{22}H_{21}N_3O_2ClF_3$: C, 58.48; H, 4.68; N, 9.30; Cl, 7.85; F, 12.61. Found: C, 58.78; H, 4.60; N, 9.01; Cl, 7.84; F, 12.42.

EXAMPLE 9

5-(4-Methoxyphenoxymethyl)-3-(4-chlorophenyl)-3-(1H-imidazol-1-ylmethyl)-2-methylisoxazolidine (4, $R^1=4$—Cl, $R^2=4$—$OCH_3$)

Compound 4 ($R^1=4$—Cl, $R^2=4$—$OCH_3$) was prepared by a procedure similar to that described in Example 1 by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl), and treating the latter with 4-methoxyphenyl ally ether (3, $R^2=4$—$OCH_3$). The resulting cis- and trans-diastereomeric mixture of compound 4 ($R^1=4$—Cl, $R^2=4$—$CH_3$) was flash-chromatographed on neutral silica gel using a 98:2 by volume mixture of dichloromethane and methanol as eluent.

Isomer A has a melting point of 140°–145° C. (ethyl acetate).

Anal. Calcd for $C_{22}H_{24}N_3O_3Cl$: C, 63.84; H, 5.84; N, 10.15; Cl, 8.57. Found: C, 64.16; H, 5.95; N, 10.16; Cl, 8.60.

EXAMPLE 10

5-(4-Methylphenoxymethyl)-3-(4-chlorophenyl)-3-(1H-imidazol-1-ylmethyl)-2-methylisoxazolidine (4, $R^1=4$—Cl, $R^2=4$—$CH_3$)

Compound 4 ($R^1=4$—Cl, $R^2=4$—$CH_3$) was prepared by a procedure similar to that described in Example 1 by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl), and treating and latter with 4-methylphenyl allyl ether (3, $R^2=4$—$CH_3$). The resulting cis- and trans-diastereomeric mixture of compound 4 ($R^1=4$—Cl, $R^2=4$—$CH_3$) was flash-chromatographed on neutral silica gel using a 98:2 by volume mixture of dichloromethane and methanol as eluent.

Isomer A has a melting point of 115°–123° C. (ethyl acetate).

Isomer B has a melting point of 111°–134° C. (ethyl acetate).

Anal. Calcd for $C_{22}H_{24}ClN_3O_2$: C, 66.41; H, 6.08; N, 10.56; Cl, 8.91. Found C, 65.70; H, 6.15; N, 10.35; Cl, 9.10.

EXAMPLE 11

5-(2,5-Dichlorophenoxymethyl)-3-(4-chlorophenyl)-3-(1H-imidazol-1-ylmethyl)-2-methylisoxazolidine (4, $R^1=4$—Cl, $R^2=2,6$—Cl$_2$)

Compound 4 ($R^1=4$—Cl, $R^2=2,6$—Cl$_2$) was made by a procedure similar to that described in Example 1 by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl), and treating the latter with 2,6-dichlorophenyl allyl ether (3, $R^2=2,6$—Cl$_2$). The resulting cis- and trans-diastereomeric mixture of compound 4 ($R^1=4$—Cl, $R^2=2,6$—Cl$_2$) was flash-chromatographed on neutral silica gel using a 95:5 by volume mixture of dichloromethane and methanol as eluent.

Isomer A has a melting point of 144°–48° C. (ethyl acetate).

Anal. Calcd for $C_{21}H_{20}N_3O_2Cl_3$: C,55.71; H, 4.45; N, 92.8; Cl, 23.49. Found: C, 55.72; H, 4.58; N, 9.22; Cl, 23.14.

EXAMPLE 12

5-(2,4-Dichlorophenoxymethyl)-3-(4-chlorophenyl)-3-(1H-imidazol-1-ylmethyl)-2-methylisoxazolidine (4, $R^1=4$—Cl, $R^2=2,4$—Cl$_2$)

Compound 4 ($R^1=4$—Cl, $R^2=2,4$—Cl$_2$) was obtained by a procedure similar to that described in Example 1 by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl), and treating the latter with 2,4-dichlorophenyl allyl ether (3, $R^2=2,4$—Cl$_2$). The resulting cis- and trans-diastereomeric mixture of compound 4 ($R^1=4$—Cl, $R^2=2,4$—Cl$_2$) was flash-chromatographed on neutral silica gel using ethyl acetate as eluent.

Isomer A has a melting point of 145°–148° C. (ethyl acetate).

Anal. Calcd for $C_{21}H_{20}N_3O_2Cl_3$: C, 55.71; H, 4.45; N, 9.28; Cl, 23.49. Found C, 55.55; H, 4.51; N, 9.18; Cl, 23.32.

EXAMPLE 13

5-(2-Nitrophenoxymethyl)-3-(4-chlorophenyl)-3-(1H-imidazol-1-ylmethyl)-2-methylisoxazolidine (4, $R^1=4$—Cl, $R^2=2$—NO$_2$)

Compound 4 ($R^1=4$—Cl, $R^2=2$—NO$_2$) was made by a procedure similar to that described in Example 1 by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl) and treating the latter with 2-nitrophenyl allyl ether (3, $R^2=2$—NO$_2$). The resulting cis- and trans-diastereomeric mixture of compound 4 ($R^1=4$—Cl, $R^2=2$—NO$_2$) was flash-chromatographed on neutral silica gel using a 98:2 by volume mixture of dichloromethane and methanol as eluent.

Isomer A has a melting point of 135°–138° C. (ethyl acetate).

Anal. Calcd for $C_{21}H_{21}N_4O_4Cl$: C, 58.81; H, 4.94; N, 13.06; Cl, 8.27. Found: C, 58.88; H, 4.98; N, 13.12; Cl, 8.38.

EXAMPLE 14

5-(4-Fluorophenoxymethyl)-3-(4-chlorophenyl)-3-(1H-imidazol-1-ylmethyl)-2-methylisoxazolidine (4, $R^1=4$—Cl, $R^2=4$—F)

Compound 4 ($R^1=4$—Cl, $R^2=4$—F) was obtained by a procedure similar to that described in Example 1 by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl), and treating and latter with 4-fluorophenyl allyl ether (3, $R^2=4$—F). The resulting cis- and trans-diastereomeric mixture of compound 4 ($R^1=4$—Cl, $R^2=4$—F) was flash-chromatographed on neutral silica gel using a 98:2 by volume mixture of dichloromethane and methanol as eluent.

Isomer A has a melting point of 121°–126° C. (ethyl acetate).

Calcd for $C_{21}H_{21}N_3O_2ClF$: C, 62.76; H, 5.27; N, 10.46; Cl, 8.82; F, 4.73. Found: C, 62.72; H, 5.26; N, 10.43; Cl, 8.66; F, 4.68.

EXAMPLE 15

5-(4-Chlorophenoxy)methyl-3-(4-chloro-3-methylphenyl)-3-(1H-imidazol-1-ylmethyl)-2-methylisoxazoldine (4,$R^1=4$—Cl, 3—CH$_3$, $R^2=4$—Cl).

Compound 4 ($R^1=4$—Cl, 3—CH$_3$, $R^2=4$—Cl) was made by a procedure similar to that described in Example 1 by reacting 2-(1H-imidazol-1-yl)-4'-chloro-3'methylacetophenone (1, $R^1=4$—Cl, 3—CH$_3$) with N-methylhydroxylamine hydrochloride to form the corresponding nitrone derivative 2 ($R^1=4$—Cl, 3—CH$_3$), and treating the latter with 4-chlorophenyl allyl ether (3, $R^2=4$—Cl). The resulting cis- and trans-diastereomeric mixture of compound 4 ($R^1=4$—Cl, 3—CH$_3$, $R^2=4$—Cl) was flash-chromatographed on neutral silica gel using a 98:2 by volume mixture of chloroform and methanol as eluent.

Isomer A has a melting point of 142°–146° C. (ethyl acetate).

Anal. Calcd for $C_{22}H_{23}Cl_2N_3O_2$: C, 61.12; H, 5.36; N, 9.72; Cl, 16.40. Found: C, 61.08; H, 5.45; N, 9.72; Cl, 16.34.

EXAMPLE 16

5-(4-Chlorophenoxy)methyl-3-(1H-imidazol-1-ylmethyl)-3-(3-methoxyphenyl)-2-methylisoxazolidine (4, $R^1=3$—CH$_3$O, $R^2=4$—Cl)

Compound 4 ($R^1=3$—CH$_3$O, $R^2=4$—Cl) was made by a procedure similar to that described in Example 1 by reacting 2-(1H-imidazol-1-yl)-3'-methoxyacetophenone (1, $R^1=3$—CH$_3$O) with N-methylhydroxylamine hydrochloride to form the corresponding nitrone derivative 2 ($R^1=3$—CH$_3$O) and treating the latter with 4-chlorophenyl allyl ether (3, $R^2=4$—Cl). The resulting cis- and trans-diastereomeric mixture of compound 4 ($R^1=3$—CH$_3$O, $R^2=4$—Cl) was flash-chromatographed on neutral silica gel using a 98:2 by volume mixture of chloroform and methanol as eluent.

Isomer A has a melting point of 92°–95° C. (ethyl ether).

Anal. Calcd for $C_{22}H_{24}ClN_3O_3$: C, 63.84; H, 5.84; N, 10.15; Cl, 8.57. Found: C, 63.61; H, 5.90; N, 10.14; Cl, 8.55.

EXAMPLE 17

5-(4-Chlorophenoxy)methyl-3-(1H-imidazol-1-ylmethyl)-2-methyl-3-(3-methylphenyl) isoxazolidine (4, $R^1=3-CH_3$, $R^2=4-Cl$)

Compound 4 ($R^1=3-CH_3$, $R^2=4-Cl$) was made by a procedure similar to that described in Example 1 by reacting 2-(1H-imidazol-1-yl)-3'-methylacetophenone (1, $R^1=3-CH_3$) with N-methylhydroxylamine hydrochloride to form the corresponding nitrone derivative 2 ($R^1=3-CH_3$), and treating the latter with 4-chlorophenyl allyl ether (3, $R^2=4-Cl$). The resulting cis- and trans-diastereomeric mixture of compound 4 ($R^1=3-CH_3$, $R^2=4-Cl$) was flash-chromatographed on neutral silica gel using a 99:1 by volume mixture of chloroform and methanol as eluant.

Isomer A has a melting point of 122°–124° C. (ethyl acetate).

Anal. Calcd. for $C_{22}H_{24}ClN_3O_2$: C, 66.41; H, 6.08; N, 10.56; Cl, 8.91. Found: C, 66.45; H, 6.14; N, 10.63; Cl, 9.09.

EXAMPLE 18

5-[2-(4-Chlorophenoxy)ethyl]-3-(4-chlorophenyl)-3-(1H-imidazol-1-ylmethyl)-2-methylisoxazolidine (6, $R^1=R^2=4-Cl$, n=2)

Compound 6 ($R^1=4-Cl$, $R^2=4-Cl$, n=2) was prepared by a procedure similar to that described in Example 1 by reacting 2-(1H-imidazol-1-yl)-4'-chloroacetophenone (1, $R^1=4-Cl$) with N-methylhydroxylamine hydrochloride to form the corresponding nitrone derivative 2 ($R^1=4-Cl$), and treating the latter with 1-(3-butenyloxo)-4-chlorobenzene (5, $R^2=4-Cl$, n=2). The resulting cis- and trans-diastereomeric mixture of compound 6 ($R^1=4-Cl$, $R^2=4-Cl$, n=2) was flash-chromatographed on neutral silica gel using a 98:2 by volume mixture of chloroform and methanol as eluent.

Isomer A has a melting point of 103°–105° C. (ethyl acetate).

Anal. Calcd for $C_{22}H_{23}Cl_2N_3O_2$: C, 61.12; H, 5.36; N, 9.72; Cl, 16.40. Found: C, 61.08; H, 5.44; N, 9.64; Cl, 16.50.

EXAMPLE 19

5-[3-(4-Chlorophenoxy)propyl]-3-(4-chlorophenyl)-3-(1H-imidazol-1-ylmethyl)-2-methylisoxazolidine (6, $R^1=R^2=4-Cl$, n=3)

Compound 6 ($R^1=R^2=4-Cl$, n=3) was prepared by a procedure similar to that described in Example 1 by reacting 2-(1H-imidazol-1-yl)-4'-chloroacetophenone (1, R=4-Cl) with N-methylhydroxylamine hydrochloride to form the corresponding nitrone derivative 2 ($R^1=4-Cl$), and treating the latter with 1-(4-pentenyloxy)-4-chlorobenzene (5, $R^2=4-Cl$, n=3). The resulting cis- and trans-diasteriomeric mixture of compound 6 ($R^1=R^2=4-Cl$, n=3) was flash-chromatographed on neutral silica gel using a 98:2 by volume mixture of chloroform and methanol as eluent.

Isomer A has a melting point of 118°–123° C. (ethyl acetate).

Anal. Calcd. for $C_{23}H_{25}Cl_2N_3O_2$: C, 61.89; H, 5.65; N, 9.41; Cl, 15.88. Found: C, 6.99; H, 5.71; N, 9.42; Cl, 15.47.

EXAMPLE 20

3-(4-Chlorophenyl)-5-[3-(4-fluorophenoxy)propyl]-3-(1H-imidazol-1-ylmethyl)-2-methylisoxazolidine (6, $R^1=4-Cl$, $R^2=4-F$, n=3)

Compound 6 of ($R^1=4-Cl$, $R^2=4-F$, n=3) was prepared by a procedure similar to that described in Example 1 by reacting 2-(1H-imidazol-1-yl)-4'-chloroacetophenone (1, $R^1=4-Cl$) with N-methylhydroxylamine hydrochloride to form the corresponding nitrone derivative 2 ($R^1=4-Cl$), and treating the latter with 1-(4-pentenyloxy)-4-fluorobenzene (5, $R^2=4-F$, n=3). The resulting cis- and trans-diastereomeric mixture of compound 6 ($R^1=4-Cl$, $R^2=4-F$, n=3) was flash-chromatographed on neutral silica gel using a 98:2 by volume mixture of chloroform and methanol as eluent.

Isomer A has a melting point of 116°–120° C. (ethyl acetatehexane, 1:1 by volume).

EXAMPLE 21

5-[3-(4-Fluorophenoxy)propyl]-3-(4-fluorophenyl)-3-(1H-imidazol-1-ylmethyl)-2-methylisoxazolidine (6, $R^1=R^2=4-F$, n=3)

Compound 6 ($R^1=R^2=4-F$, n=3) was prepared by a procedure similar to that described in Example 1 by reacting 2-(1H-imidazol-1-yl)-4'-fluoroacetophenone (1, $R^1=4-F$) with N-methylhydroxylamine hydrochloride to form the corresponding nitrone derivative 2 ($R^1=4-F$), and treating the latter with 1-(4-pentenyloxy)-4-fluorobenzene (5, $R^2=4-F$, n=3). The resulting cis- and trans-diastereomeric mixture of compound 6 ($R^1=R^2=4-F$, n=3) was flash-chromatographed on neutral silica gel using a 98:2 by volume mixture of chloroform and methanol as eluent.

Isomer A has a melting point of 96°–100° C. (ethyl acetatehexane, 1:1 by volume).

EXAMPLE 22

5-[(4-Fluorophenoxy)methyl]-3-(1H-imidazol-1-ylmethyl)-2-methyl-3-phenylisoxazolidine (4, $R^1=H$, $R^2=4-F$)

Compound 4 ($R^1=H$, $R^2=4-F$) was made by a procedure similar to that described in Example 1 by reacting 2-(1H-imidazol-1-yl)acetophenone (1, $R^1=H$) with N-methylhydroxylamine hydrochloride to form the corresponding nitrone derivative 2 ($R^1=H$), and treating the latter with 4-fluorophenyl allyl ether (3, $R^2=4-F$). The resulting cis- and trans-diastereomeric mixture of compound 4 ($R^1=H$, $R^2=4-F$) was flash-chromatographed on neutral silica gel using ethyl acetate as eluent.

Isomer A has a melting point of 115°–117° C. (ethyl acetate).

Anal. Calcd for $C_{21}H_{22}FN_3O_2$: C, 68.65; H, 6.04; N, 11.44; F, 5.17. Found: C, 68.54; H, 6.16; N, 11.41; F, 5.15.

Isomer B has a melting point of 111°–115° C. (ethyl acetate).

Anal. Calcd for $C_{21}H_{22}FN_3O_2$: C, 68.65; H, 6.04; N, 11.44; F, 5.17. Found: C, 69.03; H, 6.13; N, 11.38; F, 5.22.

EXAMPLE 23

5-[(4-Chloro-3-methylphenoxy)methyl]-3-(1H-imidazol-1-ylmethyl)-2-methyl-3-phenylisoxazolidine (4, $R^1$=H, $R^2$=4—Cl, 3—$CH_3$)

Compound 4 ($R^1$=H, $R^2$=4—Cl, 3—$CH_3$) was prepared by a method similar to that described in Example 1 by reacting 2-(1H-imidazol-1-yl)acetophenone (1,$R^1$=H) with N-methylhydroxylamine hydrochloride to form the corresponding nitrone derivative 2 ($R^1$=H), and treating the latter with 4-chloro-3-methylphenyl allyl ether (3, $R^2$=4—Cl, 3—$CH_3$). The resulting cis- and trans-diastereomeric mixture of compound 4 ($R^1$=H, $R^2$=4—Cl, 3—$CH_3$) was flash-chromatographed on neutral silica gel using a 98:2 by volume mixture of chloroform and methanol as eluent.

Isomer A a has melting point of 110°–120° C. (ethyl acetate).

Anal. Calcd for $C_{22}H_{24}ClN_3O_2$: C, 66.41; H, 6.08; N, 10.52; Cl, 8.91. Found: C, 66.38; H, 6.19; N, 10.46; Cl, 8.87.

EXAMPLE 24

3-(4-Fluorophenyl)-3-(1H-imidazol-1-ylmethyl)-2-methyl-5-(phenoxymethyl)isoxazolidine (4, $R^1$=4—F, $R^2$=H)

Compound 4 ($R^1$=4—F, $R^2$=H) was made by a procedure similar to that described in Example 1 by reacting 4'-fluoro-2-(1H-imidazol-1-yl)acetophenone (1, $R^1$=4—F) with N-methylhydroxylamine hydrochloride to form the corresponding nitrone derivative 2 ($R^1$=4—F), and treating the latter with phenyl allyl ether (3, $R^2$=H). The resulting cis- and trans-diastereomeric mixture of compound 4 ($R^1$=4—F, $R^2$=H) was flash-chromatographed on neutral silica gel using a 98:2 by volume mixture of chloroform and methanol.

Isomer A has a melting point of 164°–166° C. (isopropanol).

Anal. Calcd for $C_{21}H_{22}FN_3O_2$: C, 68.65; H, 6.04; N, 11.44; F, 5.17. Found: C, 68.62; H, 5.96; N, 11.37; F, 5.12.

EXAMPLE 25

5-[(4-Fluorophenoxy)methyl]-3-(4-fluorophenyl)-3-(1H-imidazol-1-ylmethyl)-2-methylisoxazolidine (4, $R^1$=$R^2$=4—F)

Compound 4 ($R^1$=$R^2$=4—F) was made by a procedure similar to that described in Example 1 by reacting 4'-fluoro-2-(1H-imidazol-1-yl) acetophenone (1, $R^1$=4—F) with N-methylhydroxylamine hydrochloride to form the corresponding nitrone derivative 2 ($R^1$=4—F), and treating the latter with 4-fluorophenyl allyl ether (3, $R^2$=4—F). The resulting cis- and trans-diastereomeric mixture of compound 4 ($R^1$=$R^2$=4—F) was flash-chromatographed on neutral silica gel using ethyl acetate as the eluent.

Isomer A has a melting point 141°–143° C. (ethyl acetate).

Anal. Calcd for $C_{21}H_{21}F_2N_3O_2$: C, 65.44; H, 5.49; N, 10.90; F, 9.86. Found: C, 65.84; H, 5.38; N, 10.88; F, 9.55.

EXAMPLE 26

3-(1H-Imidazol-1-ylmethyl)-5-[(4-methoxyphenoxy)methyl]-3-(4-methoxyphenyl)-2-methylisoxazolidine (4, $R^1$=$R^2$=4—$OCH_3$)

Compound 4 ($R^1$=$R^2$=4—$OCH_3$) was made by a procedure similar to that described in Example 1 by reacting 2-(1H-imidazol-1-yl)-4'-methoxyacetophenone (1, $R^1$=4—$OCH_3$) with N-methylhydroxylamine hydrochloride to form the corresponding nitrone derivative 2 ($R^1$=4—$OCH_3$), and treating the latter with 4-methoxyphenyl allyl ether (3, $R^2$=4—$OCH_3$). The resulting cis- and trans-diastereomeric mixture of compound 4 ($R^1$=$R^2$=4—$OCH_3$) was flash-chromatographed on neutral silica gel using a 98:2 by volume mixture of methylene chloride and methanol as eluent.

Isomer A has a melting point of 96°–101° C. (ethyl acetate).

Anal. Calcd for $C_2H_{27}N_3O_4$: C, 67.46; H, 6.65; N, 10.26. Found C, 67.43; H, 6.64; N, 10.20.

EXAMPLE 27

5-[(4-Acetamidophenoxy)methyl]-3-(4-chlorophenyl)-3-(1H-imidazol-1-ylmethyl)-2-methylisoxazolidine (4, $R^1$=4—Cl, $R^2$=NHAc)

Compound 4 ($R^1$=4—Cl, $R^2$=NHAc) was prepared by a method similar to that described in Example 1 by reacting 4'-chloro-2-(1H-imidazol-1-yl) acetophenone (1, $R^1$=4—Cl) with N-methylhydroxylamine hydrochloride to form the corresponding nitrone derivative 2 ($R^1$=4—Cl), and treating the latter with 4-acetamidophenyl allyl ether (3, $R^2$=4-NHAc). The resulting cis- and trans-diastereomeric mixture of compound 4 ($R^1$=4—Cl, $R^2$=4-NHAc) was flash-chromatographed on neutral silica gel using a 98:2 by volume mixture of chloroform and methanol as eluent.

Isomer A has a melting point of 181°–186° C. (ethyl acetate).

Anal. Calcd for $C_{23}H_{25}ClN_4O_3$: C, 62.65; H, 5.72; N, 12.71; Cl, 8.04. Found: C, 62.52; H, 5.76; N, 12.58; Cl, 8.09.

EXAMPLE 28

Salts of 5-(4-Chlorophenoxymethyl)-3-(4-chlorophenyl)-3-(1H-imidazol-1-ylmethyl)-2-methylisoxazolidine (4, $R^1$=$R^2$=4—Cl)

Salts of the title compound 4 were prepared by dissolving the compound in a 10:1 by volume mixture of ethanol and the appropriate concentrated acid, evaporating the solvent and then recrystallizing the crude salt from methanol-ether (1:3 by volume in the case of the HCl salt), and ethanol in the case of the $HNO_3$ salt.

Isomer A·2HCl has a melting point of 170°–183° C.

Anal. Calcd for $C_{21}H_{23}Cl_4N_3O_2$: C, 51.35; H, 4.72; N, 8.55; Cl, 28.87. Found, C, 51.45; H, 4.84; N, 8.50; Cl, 27.72.

Isomer A·$HNO_3$ has a melting point of 165°–167° C.

Anal. Calcd for $C_{21}H_{22}Cl_2N_4O_5$: C, 52.40; H, 4.61; N, 11.67; Cl, 14.73. Found: C, 52.51; H, 4.70; N, 11.67; Cl, 14.84.

Salts with other acids and salts of other compounds of the invention can be prepared in a similar manner.

We claim:

1. A compound of the formula:

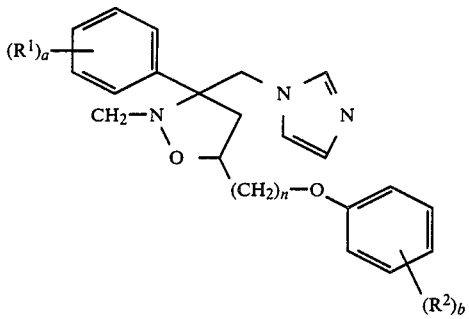

or a pharmaceutically acceptable acid addition salt thereof, in the form of their enantiomers or mixtures of their enantiomers including diastereoisomeric pairs of such enantiomers, wherein;

a = 1 or 2, b = 1 or 2, $R^1$ is selected from hydrogen, lower alkyl, lower alkoxy, halogen, and combinations thereof, provided that the ortho position is hydrogen, $R^2$ is selected from hydrogen, lower alkyl, lower alkoxy, halogen, trifluoromethyl, nitro, acetamido, and combinations thereof, and the alkyl moiety $(CH_2)n$ represents a branched or unbranched chain were n = 1 to 8.

2. The compound of claim 1 wherein the compound is 5-(4-chlorophenoxymethyl)-3-(4-chlorophenyl)-3-(1H-imidazol-1-ylmethyl)-2-methylisoxazolidine.

3. The compound of claim 1 wherein the compound is 5-(4-chlorophenoxymethyl)-3-(4-methoxyphenyl)-3-(1H-imidazol-1-ylmethyl)-2-methylisoxazolidine.

4. The compound of claim 1 wherin the compound is 5-(4-chlorophenoxymethyl)-3-(4-methylphenyl)-3-(1H-imidazol-1-ylmethyl)-2-methylisoxazolidine.

5. The compound of claim 1 wherein the compound is 5-(4-chlorophenoxymethyl)-3-(4-fluorophenyl)-3-(1H-imidazol-1-ylmethyl)-2-methylisoxazolidine.

6. The compound of claim 1 wherein the compound is 5-(4-chlorophenoxymethyl)-3-phenyl-3-(1H-imidazol-1-ylmethyl)-2-methylisoxazolidine.

7. The compound of claim 1 wherein the compound is 5-(4-chlorophenoxymethyl)-3-(3,4-dichlorophenyl)-3-(1H-imidazol-1-ylmethyl)-2-methylisoxazolidine.

8. The compound of claim 1 wherein the compound is 5-phenoxymethyl-3-phenyl-3-(1H-imidazol-1-ylmethyl)-2-methylisoxazolidine.

9. The compound of claim 1 wherein the compound is 5-[3-(trifluoromethyl)phenoxymethyl]-3-(4-chlorophenyl)-3-(1H-imidazol-1-ylmethyl)-2-methylisoxazolidine.

10. The compound of claim 1 wherein the compound is 5-(4-methoxyphenoxymethyl)-3-(4-chlorophenyl)-3-(1H-imidazol-1-ylmethyl)-2-methylisoxazolidine.

11. The compound of claim 1 wherein the compound is 5-(4-methylphenoxymethyl)-3-(4-chlorophenyl)-3-(1H-imidazol-1-ylmethyl)-2-methylisoxazolidine.

12. The compound of claim 1 wherein the compound is 5-(2,6-dichlorophenoxymethyl)-3-(4-chlorophenyl)-3-(1H-imidazol-1-ylmethyl)-2-methylisoxazolidine.

13. The compound of claim 1 wherein the compound is 5-(2,4-dichlorophenoxymethyl)-3-(4-chlorophenyl)-3-(1H-imidazol-1-ylmethyl)-2-methylisoxazolidine.

14. The compound of claim 1 wherein the compound is 5-(2-nitrophenoxymethyl)-3-(4-chlorophenyl)-3-(1H-imidazol-1-ylmethy)-2-methylisoxazolidine.

15. The compound of claim 1 wherein the compound is 5-(4-fluorophenoxymethyl)-3-(4-chlorophenyl)-3-(1H-imidazol-1-ylmethyl)-2-methylisoxazolidine.

16. The compound of claim 1 wherein the compound is 5-(4-chlorophenoxy)methyl-3-(4-chloro-3-methylphenyl)-3-1H-imidazol-1-yl-methyl)-2-methylisoxazolidine.

17. The compound of claim 1 wherein the compound is 5-(4-chlorophenoxy)methyl-3-(1H-imidazol-1-ylmethyl)-3-(3-methoxyphenyl)-2-methylisoxazolidine.

18. The compound of claim 1 wherein the compound is 5-(4-chlorophenoxy)methyl-3-(1H-imidazol-1-ylmethyl)-2-methyl-3-(3-methylphenyl)isoxazolidine.

19. The compound of claim 1 wherein the compound is 5-[2-(4-chlorophenoxy)ethyl]-3-(4-chlorophenyl)-3H-imidazol-1-ylmethyl)-2-methylisoxazolidine.

20. The compound of claim 1 wherein the compound is 5-[3-(4-chlorophenoxy)propyl]-3-(4-chlorophenyl)-3-(1H-imidazol-1-ylmethyl)-2-methylisoxazolidine.

21. The compound of claim 1 wherein the compound is 3-(4-chlorophenyl)-5-[3-(4-fluorophenoxy)propyl]-3-(1H-imidazol-1-ylmethyl)-2-methylisoxazolidine.

22. The compound of claim 1 wherein the compound is 5-[3-(4-fluorophenoxy)propyl]-3-(4-fluorophenyl)-3-(1H-imidazol-1-ylmethyl)-2-methylisoxazolidine.

23. The compound of claim 1 wherein the compound is 5-[(4-fluorophenoxy)methyl]-3-(1H-imidazol-1-ylmethyl)-2-methyl-3-phenylisoxazolidine.

24. The compound of claim 1 wherein the compound is 5-[(4-chloro-3-methylphenoxy)methyl]-3-(1H-imidazol-1-ylmethyl)-2-methyl-3-phenylisoxazolidine.

25. The compound of claim 1 wherein the compound is 3-(4-fluorophenyl)-3-(1H-imidazol-1-ylmethyl)-2-methyl-5-(phenoxymethyl)isoxazolidine.

26. The compound of claim 1 wherein the compound is 5-[(4-fluorophenoxy)methyl]-3-(4-fluorophenyl)-3-(1H-imidazol-1-ylmethyl)-2-methylisoxazolidine.

27. The compound of claim 1 wherein the compound is 3-(1H-imidazol-1-ylmethyl)-5-[(4-methoxyphenoxy)methyl]-3-(4-methoxyphenyl)-2-methylisoxazolidine.

28. The compound of claim 1 wherein the compound is 5-[(4-acetamidophenoxy)methyl]-3-(4-chlorophenyl)-3-(1H-imidazol-1-ylmethyl)-2-methylisoxazolidine.

29. The compound of claim 1 wherein the compound is a diastereoisomeric pair of enantiomers.

* * * * *

UNITED STATES PATENT AND TRADEMARK OFFICE
CERTIFICATE OF CORRECTION

PATENT NO. : 4,723,021

DATED : February 2, 1988

INVENTOR(S) : Vassil St. Georgiev et al.

It is certified that error appears in the above-identified patent and that said Letters Patent are hereby corrected as shown below:

In column 1 at line 23, in column 2 at line 11, and in claim 1 column 15 at line 6 "$CH_2$" attached to nitrogen in the structural formula should read -- $CH_3$ --.

In claim 19 second line "3H" should read -- 3-(1H --.

Signed and Sealed this

Nineteenth Day of July, 1988

Attest:

DONALD J. QUIGG

*Attesting Officer*    *Commissioner of Patents and Trademarks*